United States Patent [19]

Hölzemann et al.

[11] Patent Number: 4,709,010

[45] Date of Patent: Nov. 24, 1987

[54] PEPTIDES USEFUL FOR INHIBITION OF RENIN

[75] Inventors: Günter Hölzemann, Seeheim; Peter Raddatz; Alfred Jonczyk, both of Darmstadt; Claus J. Schmitges, Gross-Umstadt, all of Fed. Rep. of Germany

[73] Assignee: Merck Patent Gesellschaft mit beschrankter Haftung, Darmstadt, Fed. Rep. of Germany

[21] Appl. No.: 789,286

[22] Filed: Oct. 18, 1985

[30] Foreign Application Priority Data

Oct. 20, 1984 [DE] Fed. Rep. of Germany ....... 3438545

[51] Int. Cl.$^4$ .................... C07C 103/52; A61K 37/02; A61K 49/00
[52] U.S. Cl. .................................. 530/323; 530/330; 530/331; 530/332; 514/17; 514/18
[58] Field of Search ................. 260/998.2, 998.22; 530/331, 330, 332, 323; 514/18, 17

[56] References Cited

U.S. PATENT DOCUMENTS

| | | | |
|---|---|---|---|
| 4,424,207 | 1/1984 | Szelke et al. | 530/327 |
| 4,609,643 | 9/1986 | Szelke et al. | 530/328 |
| 4,638,047 | 1/1987 | Szelke et al. | 530/328 |
| 4,645,759 | 2/1987 | Luly et al. | 530/331 |
| 4,650,661 | 3/1987 | Szelke et al. | 530/323 |
| 4,652,551 | 3/1987 | Luly et al. | 514/18 |
| 4,657,931 | 4/1987 | Baran et al. | 530/331 |
| 4,663,310 | 5/1987 | Bock et al. | 530/330 |
| 4,665,055 | 5/1987 | Evans | 514/18 |
| 4,666,888 | 5/1987 | Raddatz et al. | 514/18 |
| 4,668,770 | 5/1987 | Boger et al. | 530/331 |

FOREIGN PATENT DOCUMENTS 77028  4/1983  European Pat. Off. .
84/03044  8/1984  PCT Int'l Appl. .

OTHER PUBLICATIONS

Chem. Abstracts, vol. 97, (1982), 39405p.

*Primary Examiner*—Delbert R. Phillips
*Assistant Examiner*—Nathan M. Nutter
*Attorney, Agent, or Firm*—Millen & White

[57] ABSTRACT

New peptides of the formula I

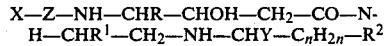

$$X-Z-NH-CHR-CHOH-CH_2-CO-NH-CHR^1-CH_2-NH-CHY-C_nH_{2n}-R^2 \quad I$$

in which
X is H, $R^3-O-CH_2-CO-$, $R^3-O-CO-$, $R^3-CH_2-O-CO-$ or $R^3-C_mH_{2m}-CO-$,
Z is 1 to 4 aminoacid residues which are bonded together in the manner of peptides and are selected from the group comprising Abu, Ala, Arg, Asn, Dab, Gln, Gly, His, Ile, Leu, Lys, Met, NLeu, Orn, Phe, Pro, Trp, Tyr and Val,
R is A, Ar-alkyl (in which the group -alkyl contains 1-4 C atoms) or cycloalkyl-alkyl having 4-11 C atoms,
$R^1$ is H or A,
Y is H, A, $-C_pH_{2p}-OR^4$, $-C_pH_{2p}-NHR^4$, $-COOR^4$, $-CONHR^4$ or $-CONA_2$,
$R^2$ is A, cycloalkyl having 3-7 C atoms, Ar, pyridyl, indolyl, imidazolyl, piperidyl, N-benzylpiperidyl or piperazinyl,
$R^3$ is A, cycloalkyl having 3-7 C atoms or Ar,
$R^4$ is H, A or cycloalkyl having 3-7 C atoms,
A is alkyl having 1-6 C atoms,
Ar is phenyl which is unsubstituted or substituted once or several times by A, AO, F, Cl, Br, I, $CF_3$ and/or $NH_2$, or is unsubstituted naphthyl, and
m, n and p each are 0, 1, 2, 3, 4 or 5, and their salts inhibit the activity of the renin in human plasma.

19 Claims, No Drawings

PEPTIDES USEFUL FOR INHIBITION OF RENIN

BACKGROUND OF THE INVENTION

This invention relates to new peptides. Similar compounds are disclosed in European Pat. No. A-77,028.

SUMMARY OF THE INVENTION

It is an object of this invention to provide new compounds with valuable properties, in particular those which can be used for the preparation of medicaments. Upon further study of the specification and appended claims, further objects and advantages of this invention will become apparent to those skilled in the art.

These objects have been achieved by providing new peptides of formula I

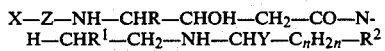

$$X-Z-NH-CHR-CHOH-CH_2-CO-NH-CHR^1-CH_2-NH-CHY-C_nH_{2n}-R^2 \quad I$$

in which

X is H, $R^3-O-CH_2-CO-$, $R^3-O-CO-$, $R^3-CH_2-O-CO-$ or $R^3-C_mH_{2m}-CO-$,

Z is 1 to 4 aminoacid residues which are bonded together in the manner of peptides and are selected from the group comprising Abu, Ala, Arg, Asn, Dab, Gln, Gly, His, Ile, Leu, Lys, Met, NLeu, Orn, Phe, Pro, Trp, Tyr and Val, R is A, Ar-alkyl (In which the group -alkyl contains 1–4 C atoms) or cycloalkyl-alkyl having 4–11 C atoms.

$R^1$ is H or A,

Y is H, A, $-C_pH_{2p}-OR^4$, $-C_pH_{2p}-NHR^4$, $-COOR^4$, $-CONHR^4$ or $-CONA_2$, $R^2$ is A, cycloalkyl having 3–7 C atoms, Ar, pyridyl, indolyl, imidazolyl, piperidyl, N-benzylpiperidyl or piperazinyl, $R^3$ is A, cycloalkyl having 3–7 C atoms or Ar, $R^4$ is H, A or cycloalkyl having 3–7 C atoms, A is alkyl having 1–6 C atoms, Ar is phenyl which is unsubstituted or substituted once or several times by A, AO, F, Cl, Br, I, $CF_3$, OH and/or $NH_2$, or is unsubstituted naphthyl, and m, n and p each are 0, 1, 2, 3, 4 or 5, and to their salts.

DETAILED DISCUSSION

It has been found that the compounds of the formula I and their salts have very valuable properties. In particular, they inhibit the activity of the renin in human plasma. This action can be demonstrated by, for example, the method of F. Fyhrquist et al., Clin.Chem. 22, 250–256 (1976). It is noteworthy that these compounds are very specific inhibitors of renin; considerably higher concentrations of these compounds are necessary for inhibition of other aspartyl proteinases (for example pepsin and cathepsin D).

The compounds can be used as active compounds in medicaments in human and veterinary medicine, in particular for the prophylaxis and treatment of cardiovascular diseases, especially of hypertension, cardiac insufficiency and hyperaldosteronism. Furthermore, the compounds can be used for diagnostic purposes in order to determine the possible contribution of the renin activity to the maintenance of the pathological state in patients with hypertension or hyperaldosteronism.

The abbreviations of aminoacid residues used in the preceding and following text represent the residues $-NH-CHR-CO-$ (in which R has the specific meaning known for each aminoacid) of the following aminoacids:

| | |
|---|---|
| Abu | 2-aminobutyric acid |
| Ala | alanine |
| Arg | arginine |
| Asn | asparagine |
| Dab | 2,4-diaminobutyric acid |
| Gln | glutamine |
| Gly | glycine |
| His | histidine |
| Ile | isoleucine |
| Leu | leucine |
| tert.Leu | tert-leucine (2-amino-3,3-dimethylbutyric acid) |
| Lys | lysine |
| Met | methionine |
| NLeu | norleucine (2-aminohexanoic acid) |
| Orn | ornithine |
| Phe | phenylalanine |
| Pro | proline |
| Sta | statine (3-hydroxy-4-amino-6-methylheptanoic acid) |
| Trp | tryptophan |
| Tyr | tyrosine |
| Val | valine. |

The term "—red—" represents a reduced peptide bond ($-CH_2-NH-$ in place of $-CO-NH-$).

The following meanings are also given:

| | |
|---|---|
| BOC | tert.-butoxycarbonyl |
| BOM | benzyloxymethyl |
| CBZ | benzyloxycarbonyl |
| DCC | dicyclohexylcarbodiimide |
| DMF | dimethylformamide |
| DNP | 2,4-dinitrophenyl |
| FMOC | 9-fluorenylmethoxycarbonyl |
| HOBt | 1-hydroxybenzotriazole |
| OMe | methyl ester |
| POA | phenoxyacetyl. |

In the preceding and following text, where the specified aminoacids can occur in several enantiomeric forms, for example as constituents of the compounds of the formula I, all these forms as well as their mixtures (for example the DL-forms) are included. The L-forms with the S-configuration are preferred. Where individual compounds are specified in the following text, the abbreviations of these aminoacids relate in each case to the L-form unless expressly stated otherwise; thus, "Sta" in the individual compounds in the following text means the residue of 3S-hydroxy-4S-amino-6-methylheptanoic acid.

In the formulae in the preceding text, A has 1–6, preferably 1, 2, 3 or 4, C atoms. A is preferably methyl, ethyl, propyl, isopropyl, butyl, isobutyl, sec.-butyl or tert.-butyl, as well as pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, or 1,1,2- or 1,2,2-trimethylpropyl.

Cycloalkyl is preferably cyclopropyl, cyclobutyl, cyclopentyl, cyclohexyl or cycloheptyl, but is also, for example, 1-, 2- or 3-methylcyclopentyl, or 1-, 2-, 3- or 4methylcyclohexyl. Cycloalkyl-alkyl is preferably cycloalkyl-methyl in particular cyclohexyl-methyl.

Ar is preferably phenyl, as well as phenyl which is substituted once or several times, in particular once, and preferably twice or three times, but also four or five times, for example o-, m- or p-tolyl, o-, m- or p-ethylphenyl, o-, m- or p-methoxyphenyl, o-, m- or p-fluorophenyl, 2,3-, 2,4-, 2,5-, 2,6-, 3,4- or 3,5-difluorophenyl, pentafluorophenyl, o-, m- or p-chlorophenyl, 2,3-, 2,4-, 2,5-, 2,6-, 3,4- or 3,5-dichlorophenyl, o-, m- or p-bromophenyl, 2,3-, 2,4-, 2,5-, 2,6-, 3,4- or 3,5-dibromophenyl, o-, m- or p-iodophenyl, o-, m- or p-trifluoromethylphenyl, o-, m- or p-hydroxyphenyl, o-, m- or p-aminophenyl, 2,3-, 2,4-, 2,5-, 2,6-, 3,4- or 3,5-dimethoxyphenyl, 3,4,5-trimethoxyphenyl, as well as preferably 4-chloro-2-methoxyphenyl, 4-hydroxy-2-methoxyphenyl, and 1- or 2-naphthyl. R is preferably isobutyl or cyclohexylmethyl.

The group —NH—CHR$^1$—CH$_2$— is a "reduced" aminoacid residue. Thus R$^1$ is preferably sec.-butyl (derived from isoleucine) or isobutyl (leucine), as well as preferably H (glycine), methyl (alanine), ethyl (2-aminobutyric acid), propyl (norvaline), isopropyl (valine) or butyl (norleucine) If R$^1$ is different from H, the chiral center —CHR$^1$— can exist in different enantiomeric forms; the S-forms of the "reduced" aminoacids from which these are derived are preferred. Unless otherwise specified, the individual compounds specified in the following text are always in the form which, in respect of the group —CHR$^1$—, corresponds to the S-form of the "reduced" aminoacid corresponding to R$^1$.

R$^2$ is preferably A, in particular methyl, cyclopropyl, cyclopentyl, cyclohexyl, phenyl, o-, m- or p-methoxyphenyl, 2,4- or 3,4-dimethoxyphenyl, o-, m- or p-fluorophenyl, 2,4- or 3,4-difluorophenyl, o-, m- or p-chlorophenyl, 2,4- or 3,4-dichlorophenyl, o-, m- or p-bromophenyl, o-, m- or p-iodophenyl, o-, m- or p-trifluoromethylphenyl, o-, m- or p-hydroxyphenyl, o-, m- or p-aminophenyl, 2-, 3- or (in particular) 4-pyridyl, 1-, 2-, (in particular) 3-, 4-, 5-, 6- or 7-indolyl, 1-, 2-, (in particular) 4- or 5-imidazolyl, 1-, 2-, 3- or (in particular) 4-piperidyl, N-benzyl-2-, -3- or (in particular) -4-piperidyl, or 1-, 2- or 3-piperazinyl.

R$^3$ is preferably A, in particular methyl, ethyl, propyl, isopropyl, butyl, isobutyl or tert.-butyl; cyclopropyl, cyclopentyl, cyclohexyl or phenyl.

R$^4$ is preferably H, methyl or ethyl.

The groups $C_nH_{2n}$ and $C_mH_{2m}$ are preferably —(CH$_2$)$_n$— and —(CH$_2$)$_m$—.

The parameters m and p are each preferably 0 or 1 and the parameter n is preferably 0, 1 or 2.

X is preferably H, POA, alkoxycarbonyl such as BOC, CBZ, alkanoyl such as acetyl, propionyl, butyryl, isobutyryl or isovaleryl, cycloalkylcarbonyl such as cyclopentylcarbonyl or cyclohexylcarbonyl, aroyl such as benzoyl, arylalkanoyl such as phenylacetyl, 2- or 3-phenylpropionyl, 2- or 3-o-, -m- or -p-fluorophenylpropionyl, 2- or 3-o-, -m- or -p-chlorophenylpropionyl, cycloalkylalkanoyl such as cyclohexylacetyl, 2- or 3-cyclohexylpropionyl. Particularly preferred radicals X are H, BOC and CBZ.

Z is preferably 1, 2 or 3, as well as 4, aminoacid residues which are bonded together in the manner of peptides, in particular the group Phe-His, also His, Pro-Phe-His or His-Pro-Phe-His, as well as preferably the groups Abu-His, Ala-His, Ala-Phe, Arg-His, Asn-His, Dab-His, Gln-His, Gly-His, 5 His, His-His, Ile-His, Leu-His, Lys-His, Met-His, NLeu-His, Orn-His, Phe-Abu, Phe-Ala, Phe-Arg, Phe-Asn, Phe-Dab, Phe-Gln, Phe-Gly, Phe-Ile, Phe-Leu, Phe-Lys, Phe-Met, Phe-NLeu, Phe-Orn, Phe-Phe, Phe-Pro, Phe-Trp, Phe-Tyr, Phe-Val, Pro-His, Trp-His, Tyr-His, Val-His, Pro-Ala-His, Pro-Ala-Phe, Pro-Phe-Ala, Pro-Phe-Phe, His-Pro-Ala-His, His-Pro-Ala-Phe, His-Pro-Phe-Ala or His-Pro-Phe-Phe.

Y is preferably H; A, in particular methyl; hydroxymethyl; COOH; COOA, in particular methoxycarbonyl or ethoxycarbonyl; CONH$_2$.

The group —NH—CHY—C$_n$H$_{2n}$—R$^2$ is preferably derived from aminoacids whose COOH group can also be in an esterified, amidated or reduced form. Accordingly, some preferred groups —NH—CHY—C$_n$H$_{2n}$—R$^2$ are:

| | |
|---|---|
| —NH—CH(COOH)—CH$_2$C$_6$H$_5$ | ("Phe—OH") |
| —NH—CH(COOCH$_3$)—CH$_2$C$_6$H$_5$ | ("Phe—OMe") |
| —NH—CH(COOC$_2$H$_5$)—CH$_2$C$_6$H$_5$ | ("Phe—OEt") |
| —NH—CH(CONH$_2$)—CH$_2$C$_6$H$_5$ | ("Phe—NH$_2$") |
| —NH—CH(CH$_2$OH)—CH$_2$C$_6$H$_5$ | ("Phe—ol") |
| —NH—CH(COOH)—CH$_2$—p-C$_6$H$_4$OH | ("Tyr—OH") |
| —NH—CH(COOCH$_3$)—CH$_2$—p-C$_6$H$_4$OH | ("Tyr—OMe") |
| —NH—CH(COOC$_2$H$_5$)—CH$_2$—p-C$_6$H$_4$OH | ("Tyr—OEt") |
| —NH—CH(CONH$_2$)—CH$_2$—p-C$_6$H$_4$OH | ("Tyr—NH$_2$") |
| —NH—CH(CH$_2$OH)—CH$_2$—p-C$_6$H$_4$OH | ("Tyr—ol") |
| —NH—CH(COOH)—CH$_2$—(4-imidazolyl) | ("His—OH") |
| —NH—CH(COOCH$_3$)—CH$_2$—(4-imidazolyl) | ("His—OMe") |
| —NH—CH(COOC$_2$H$_5$)—CH$_2$—(4-imidazolyl) | ("His—OEt") |
| —NH—CH(CONH$_2$)—CH$_2$—(4-imidazolyl) | ("His—NH$_2$") |
| —NH—CH(CH$_2$OH)—CH$_2$—(4-imidazolyl) | ("His—ol") |
| —NH—CH(COOH)—CH$_2$—(3-indolyl) | ("Trp—OH") |
| —NH—CH(COOCH$_3$)—CH$_2$—(3-indolyl) | ("Trp—OMe") |
| —NH—CH(COOC$_2$H$_5$)—CH$_2$—(3-indolyl) | ("Trp—OEt") |
| —NH—CH(CONH$_2$)—CH$_2$—(3-indolyl) | ("Trp—NH$_2$") |
| —NH—CH(CH$_2$OH)—CH$_2$—(3-indolyl) | ("Trp—ol") |

The chiral centers — CHY—in these groups can exist in different enantiomeric forms; the S-forms of the aminoacids from which they are derived are preferred. Unless otherwise specified, the individual compounds specified in the following text are, in respect of the group —CHY—, always in the form which corresponds to the S-form of the aminoacid corresponding to Y and R$^2$.

Other preferred meanings of the group —NH—CHY—C$_n$H$_{2n}$—R$^2$ are, in particular, —NH—CH$_2$—C$_n$H$_{2n}$—R$^2$, for example —NH—CH$_2$—R$^2$, —NH—(CH$_2$)$_2$—R$^2$ or —NH—(CH$_2$)$_3$—R$^2$ specifically and in particular —NH—CH$_2$—Ar, such as benzylamino, o-, m- or (in particular) p-fluorobenzylamino, o-, m- or (in particular) p-chlorobenzylamino, o-, m- or (in particular) p-bromobenzylamino, —NH—(CH$_2$)$_2$—Ar, such as 2-phenylethylamino, 2-(o-, m- or, in particular, p-methoxyphenyl)ethylamino, 2-(2,4- or 3,4-dimethoxyphenyl)ethylamino, 2-(o-, m- or, in particular, p-fluorophenyl)ethylamino, 2-(o-, m- or, in particular, p-chlorophenyl)ethylamino, 2-(o-, m- or, in particular, p-bromophenyl)ethylamino, 2-(2,4- or 3,4-difluorophenyl)ethylamino, 2-(2,4- or 3,4-dichlorophenyl)ethylamino, 2-(o-, m- or, in particular, p-hydroxyphenyl)ethylamino, 2-(1- or 2-naphthyl)ethylamino, as well as —NH—(CH$_2$)$_3$—Ar, such as 3-phenylpropylamino, furthermore, for example, 2-cyclohexylethylamino, 2-(4-pyridyl)ethylamino, 2-(3-indolyl)ethylamino, 2-(4-imidazolyl)ethylamino, 2-(4-piperidyl)ethylamino, 2-(N-benzyl-4-piperidyl)ethylamino, and 2-(1-piperazinyl)ethylamino Accordingly, the invention particularly relates to those compounds of the formula I in which at least one of the residues mentioned has one of the preferred meanings indicated above. Some preferred groups of compounds can be represented by the following part-formulae Ia to Id which correspond to the formula I but in which in Ia
X is H, alkanoyl having 2-6 C atoms, POA, BOC, CBZ, cycloalkylcarbonyl having 6 or 7 C atoms, benzoyl or 3-phenylpropionyl, Z is His, His-His, Phe-Abu, Phe-Arg, Phe-Asn, Phe-Dab, Phe-Gln, Phe-His, Phe-Leu, Phe-Lys, Phe-NLeu, Phe-Orn, Phe-Phe, Phe-Trp, Phe-Tyr, Pro-His, Pro-Phe, Trp-His, Tyr-His, Pro-Phe-His or His-Pro-Phe-His, R is isobutyl or cyclohexylmethyl, $R^1$ is H or alkyl having 1-4 C atoms, Y is H, COOH, COOCH$_3$, COOC$_2$H$_5$, CONH$_2$ or CH$_2$OH, n is 0, 1 or 2, and $R^2$ is cyclohexyl; phenyl which is unsubstituted or substituted once or twice by methoxy, F, Cl, Br or OH; naphthyl, pyridyl, indolyl, imidazolyl, piperidyl, N-benzylpiperidyl or piperazinyl;

in Ib
X is H, BOC or CBZ,

Z is Phe-His, Pro-Phe-His or His-Pro-Phe-His,

R is isobutyl or cyclohexylmethyl, $R^1$ is H or alkyl having 1-4 C atoms,

Y is H, COOCH$_3$, CONH$_2$ or CH$_2$OH, n is 0, 1 or 2, and $R^2$ is cyclohexyl; phenyl which is unsubstituted or substituted once or twice by methoxy, F, Cl, Br or OH; naphthyl, pyridyl, indolyl, imidazolyl, piperidyl, N-benzylpiperidyl or piperazinyl;

in Ic
X is H or BOC,

Z is Phe-His,

R is isobutyl or cyclohexylmethyl, $R^1$ is H or alkyl having 1-4 C atoms,

Y is H, COOCH$_3$, CONH$_2$ or CH$_2$OH, n is 0, 1 or 2, and $R^2$ is cyclohexyl; phenyl which is unsubstituted or substituted once or twice by methoxy, F, Cl, Br or OH; naphthyl, pyridyl, indolyl, imidazolyl, piperidyl, N-benzylpiperidyl or piperazinyl;

in Id
X is H or BOC,

Z is Phe-His,

R is isobutyl or cyclohexylmethyl, $R^1$ is isopropyl, isobutyl or sec.-butyl,

Y is H or CH$_2$OH, n is 1, and $R^2$ is phenyl, 4-imidazolyl or p-chlorophenyl.

The invention also relates to a process for the preparation of a peptide of the formula I, and of its salts, characterized in that it is liberated from one of its functional derivatives by treatment with a solvolizing or hydrogenolyzing agents, or in that a compound which corresponds to the formula I but in place of H atoms contains one or more additional groups which can be eliminated by hydrogenolysis, and/or —C—C— and-/or —C—N— and/or —C—O— linkages, is reduced, and in that, where appropriate, a functionally modified amino grouo in a compound of the formula I is liberated by treatment with solvolizing or hydrogenolyzing agents, and/or an ester group is reduced to a hydroxymethyl group, and/or a compound of the formula I is converted into one of its salts by treatment with an acid or base The compounds of the formula I as well as the starting materials for their preparation are otherwise prepared by methods known per se and as are described in the literature (for example in standard works such as Houben-Weyl, Methoden der Organischen Chemie (Methods of Organic Chemistry) published by Georg-Thieme, Stuttgart; also European Pat. No. A-45665, European Pat. No. A-77028, European Pat. No. A-77029 and European Pat. No. A-81783), specifically under reaction conditions which are known and suitable for the reactions specified. In this context, it is also possible to make use of variants which are known per se but which are not detailed here.

It is also possible, if desired, to form the starting materials in situ so that they are not isolated from the reaction mixture but are immediately reacted further to give the compounds of the formula I.

The compounds of the formula I are preferably obtained by liberating them from their functional derivatives by solvolysis, in particular hydrolysis, or by hydrogenolysis.

Preferred starting materials for the solvolysis or hydrogenolysis are those which contain in place of one or more free amino and/or hydroxyl groups corresponding protected amino and/or hydroxyl groups, preferably those which carry an amino protective group in place of an H atom which is bonded to an N atom, in particular those of the formula II

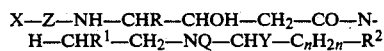

in which Q is an amino protective group.

Further preferred starting materials are those which carry an amino protective group in place of the H atom in the 1-position of an imidazole ring.

It is also possible for several—identical or different—protected amino and/or hydroxyl groups to be present in the molecule of the starting material. If the protective groups which are present differ from one another, in many cases it is possible to eliminate them selectively.

The term "amino protective group" is generally known and relates to groups which are suitable for the protection (blocking) of an amino group from chemical reactions but which can be easily removed after the desired chemical reaction has been carried out elsewhere in the molecule. Typical groups of this type are, in particular, unsubstituted or substituted acyl groups, as well as unsubstituted or substituted aryl (for example 2,4-dinitrophenyl) or aralkyl groups (for example benzyl, 4-nitrobenzyl or triphenylmethyl), as well as, in particular, benzyloxymethyl (BOM). Since the amino protective groups are removed after the desired reaction (or sequence of reactions), their nature and size are not otherwise critical; however, those having 1-20, in particular 1-8, C atoms are preferred. The term "acyl group" in the context of the present process is to be understood in its widest sense. It includes acyl groups derived from aliphatic, araliphatic, aromatic or heterocyclic carboxylic acids or sulfonic acids, as well as, in particular, alkoxycarbonyl, aryloxycarbonyl and, especially, aralkoxycarbonyl groups Examples of acyl groups of these types are alkanoyl such as acetyl, propionyl and butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, BOC and 2-iodoethoxycarbonyl; aralkyloxycarbonyl such as CBZ ("carbobenzoxy"), 4-methoxybenzyloxycarbonyl and FMOC. Preferred amino protective groups are CBZ, FMOC, benzyl, acetyl and BOM.

The term "hydroxyl protective group" is likewise generally known and relates to groups which are suitable for the protection of a hydroxyl group from chemical reactions but which can easily be removed after the desired chemical reaction has been carried out elsewhere in the molecule. Typical groups of this type are the abovementioned unsubstituted or substituted aryl, aralkyl or acyl groups, as well as alkyl groups. The nature and size of the hydroxyl protective groups are not critical since they are removed again after the desired chemical reaction or sequence of reactions; groups having 1-20, in particular 1-10, C atoms are preferred Examples of hydroxyl protective groups include benzyl, p-nitrobenzoyl, p-toluenesulfonyl and acetyl, and benzyl and acetyl are particularly preferred.

The functional derivatives of the compounds of the formula I which are to be used as starting materials can be prepared by customary methods of synthesis of aminoacids and peptides, as are described in, for example, the known standard works and patent specifications.

The liberation of the compounds of the formula I from their functional derivatives can be carried out—depending on the protective group used—for example with strong acids, preferably with trifluoroacetic acid or perchloric acid, but also with other strong inorganic acids, such as hydrochloric acid or sulfuric acid, strong organic carboxylic acids, such as trichloroacetic acid, or sulfonic acids, such as benzenesulfonic or p-toluenesulfonic acid. The presence of an additional inert solvent is possible but not always necessary. Suitable inert solvents which are preferred are organic, for example carboxylic acids such as acetic acid, ethers, such as tetrahydrofuran or dioxane, amides, such as DMF, halogenated hydrocarbons such as methylene chloride, as well as alcohols such as methanol, ethanol or isopropanol, and water. Mixtures of the abovementioned solvents are also suitable. Trifluoroacetic acid is preferably used in excess without the addition of another solvent, and perchloric acid is used in the form of a mixture of acetic acid and 70% perchloric acid in the ratio 9:1. The reaction temperatures for the cleavage are preferably between about 0° and about 50°, and between 15° and 30° (room temperature) is preferably used.

The BOC group can be eliminated with, for example and preferably, 40% trifluoroacetic acid in methylene chloride or about 3 to 5N HCl in dioxane at 15°–30°, and the FMOC group can be eliminated with an approximately 5 to 20% solution of dimethylamine, diethylamine or piperidine in DMF at 15°–30°. Elimination of the DNP group can be carried out with, for example and inter alia, an approximately 3 to 10% solution of 2-mercaptoethanol in DMF/water at 15°–30°.

Protective groups which can be removed by hydrogenolysis (for example CBZ, BOM or benzyl) can be eliminated by, for example, treatment with hydrogen in the presence of a catalyst (for example a noble metal catalyst such as palladium, preferably on a support such as charcoal). Salts of formic acid are also suitable as hydrogen donors, preferably ammonium formate. Suitable solvents for this reaction are those mentioned above, in particular, for example, alcohols such as methanol or ethanol, or amides such as DMF. The hydrogenolysis is carried out, as a rule, at temperatures between about 0° and 100° and under pressures between about 1 and 200 bar, preferably at 20°–30° and under 1-10 bar Hydrogenolysis of the CBZ group can be carried out well on, for example, 5 to 10% Pd-C in methanol at 20°–30°.

The compounds of the formula I can also be obtained by reduction of corresponding compounds which contain in place of H atoms groups which can be eliminated by hydrogenolysis, and/or additional —C—C— and/or —C—N— and/or —C—O— bonds.

Examples of suitable starting materials for the reduction are Schiff's bases of the formula X—Z—NH—CHR—CHOH—CH$_2$—CO—NH—CHR$^1$—CH=N—CHY—C$_n$H$_{2n}$—R$^2$, which can be prepared from aldehydes of the formula X—Z—NH—CHR—CHDH—CH$_2$—CO—NH—CHR$^1$—CHO and amines of the formula H$_2$N—CHY—C$_n$H$_{2n}$—R$^2$. These can advantageously be hydrogenated catalytically under the abovementioned conditions to give compounds of the formula I, for example on a noble metal catalyst, such as Pd-charcoal, in an inert solvent, such as methanol, at about 20°–30° and under 1-10 bar.

It is also possible to reduce, for example, keto compounds of the formula X—Z—NH—CHR—CO—CH$_2$—CO—NH—CHR$^1$—CH$_2$—NH—CHY—C$_n$H$_{2n}$—R$^2$ to compounds of the formula I, for example using a complex metal hydride, such as NaBH$_4$, in an inert solvent, such as methanol, at temperatures between about −10° and +30°.

Where desired, it is possible to liberate a functionally modified amino group in a compound of the formula I by solvolysis or hydrogenolysis by one of the methods described above.

Thus, in particular, a compound of the formula I in which X is different from H can be converted into a compound of the formula I (X=H), preferably by hydrogenolysis if X is CBZ, otherwise by selective solvolysis. If X is BOC, it is possible to eliminate the BOC group with, for example, HCl in dioxane at room temperature.

Furthermore, it is possible, for example, to reduce an ester of the formula I (Y=COOA) to the corresponding hydroxymethyl compound of the formula I (Y=CH$_2$OH), for example using diisobutylaluminum hydride in an inert solvent, such as dichloromethane, at temperatures between −60° and +30°.

A base of the formula I can be converted into the relevant acid addition salt with an acid. Particularly suitable acids for this reaction are those which provide physiologically acceptable salts. Thus, it is possible to use inorganic acids, for example sulfuric acid, nitric acid, hydrohalic acids such as hydrochloric acid or hydrobromic acid, phosphorus acids such as orthophosphoric acid, sulfamic acid, as well as organic acids, in particular ali-phatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane-sulfonic or ethanesulfonic acid, ethanedisulfonic acid, 2-hydroxyethanesulfonic acid, benzenesulfonic acid, p-toluene-sulfonic acid, naphthalenemonosulfonic and naphthalenedisulfonic acids, and lauryl sulfuric acid. Salts with physiologically unacceptable acids, for example picrates, can be used for the isolation and/or purification of compounds of the formula I.

An acid of the formula I can be converted into one of its physiologically acceptable metal or ammonium salts by reaction with a base. Particularly suitable salts are the sodium, potassium, magnesium, calcium and ammonium salts, as well as substituted ammonium salts, for example the dimethylammonium, diethylammonium or diisopropylammonium, monoethanolammonium, diethanolammonium and triethanolammonium, cyclohexylammonium, dicyclohexylammonium and dibenzylethylenediammonium salts, furthermore, for example, salts with N-methyl-D-glucamine or with basic aminoacids such as arginine or lysine.

The new compounds of the formula I and their physiologically acceptable salts can be used for the preparation of pharmaceutical products by converting them into a suitable administration form together with at least one vehicle or auxiliary and, if desired, together with one or more other active compound(s). The formulations thus obtained can be used as medicaments in human or veterinary medicine. Suitable vehicles are organic or inorganic substances which are suitable for enteral (for example rectal) or parenteral administration or for administration in the form of a spray for inhalation, and which do not react with the new compounds, for example water, vegetable oils, benzyl alcohols, polyethylene glycols, glycerol triacetate and other fatty acid glycerides, gelatine, and soya lecithin. Suppositories are used for rectal administration, and solutions are used for parenteral administration, preferably oily or aqueous solutions, as well as suspensions, emulsions or implants. It is possible to use for administration as a spray for inhalation sprays which contain the active compound either dissolved or suspended in a propellant gas mixture (for example fluorochlorohydrocarbons). In this case, the active compound is preferably used in the micronized form, it being possible for one or more additional physiologically tolerated solvents to be present, for example ethanol. Solutions for inhalation can be administered using customary inhalers. The new compounds can also be freeze-dried and the resulting lyophilizates can, for example, be used for the preparation of products for injection. The specified formulations can be sterilized and/or contain auxiliaries such as preservatives, stabilizers and/or wetting agents, emulsifiers, salts for affecting the osmotic pressure, buffer substances, colorants and/or aromatics. If desired, they can also contain one or more other active compounds, for example one or more vitamins.

The invention also relates to the use of the compounds of the formula I and their physiologically acceptable salts for the therapeutic treatment of the human or animal body and for combating diseases, in particular renin-dependent hypertension or hyperaldosteronism. For this purpose, the substances according to the invention are, as a rule, administered in analogy to other known and commercially available peptides, but in particular in analogy to the compounds described in European Pat. No. A-77028, preferably in doses of about 100 mg to 30 g, in particular 500 mg to 5 g, per dosage unit. The daily dose is preferably about 2 to 600 mg/kg body weight. However, the specific dose for each particular patient depends on a very wide variety of factors, for example on the activity of the specific compound used, on the age, weight, general state of health, sex, on the diet, on the time and route of administration, on the rate of elimination, on the drug combination and the severity of the particular disease to which the therapy is applied. Parenteral administration is preferred.

Renin-associated hypertension and hyperaldosteronism are effectively treated by administration of from 10 to 300 mg/k of body weight. For diagnostic purposes the novel peptides may be administered in a single dose of from 0.1 to 10 mg/kg of body weight.

Without further elaboration, it is believed that one skilled in the art can using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

In the examples which follow, "usual working up" signifies: if necessary, water is added, the pH is adjusted to 6–8, the mixture is extracted with ether or dichloromethane, and the organic phase is separated off, dried over sodium sulfate, filtered and evaporated, and purification is carried out by chromatography on silica gel and/or crystallization.

EXAMPLE 1

1 g of BOC-Phe-His(DNP)-Sta-N-[1-(N-(1-hydroxymethyl-2-phenylethyl)-N-FMOC-aminomethyl)-2-methylbutyl]-amide["BOC-Phe-His(DNP)-Sta-Ile-red-N(FMOC)-Phe-ol"; m.p 135°–138°; obtainable by condensation of BOC-Ile-OH with H-Phe-OMe in the presence of DCC/HOBt in $CH_2Cl_2$ to give BOC-Ile-Phe-OMe (m.p 118°), reduction with sodium bis(2-methoxyethoxy)aluminium hydride in benzene to give 2-(2-BOC-amino-3-methylpentylamino)-3-phenylpropanol ("BOC-Ile-red-Phe-ol"; m.p. 78°), reaction with FMOC-Cl/$NaHCO_3$ in acetone to give 2-[N-FMOC-N-(2-BOC-amino-3-methylpentyl)amino]-3-phenylpropanol["BOC-Ile-red-N(FMOC)-Phe-ol"; oil], elimination of the BOC group with 2N HCl in dioxane to give 2-[N-FMOC-N-(2-amino-3-methylpentyl)amino]-3-phenylpropanol["Ile-red-N(FMOC)-Phe-ol"], reaction with BOC-Sta-OH/DCC/HOBt to give "BOC-Sta-Ile-red-N(FMOC)-Phe-ol", cleavage to give "Sta-Ile-red-N(FMOC)-Phe-ol", reaction with BOC-His-(DNP)-OH/DCC/HOBt to give "BOC-His(DNP)-Sta-Ile-red-N(FMOC)-Phe-ol", cleavage to give "His(DNP)-Sta-Ile-red-N(FMOC)-Phe-ol" and condensation with BOC-Phe-OH/DCC/HOBt] in 20 ml of DMF, water is added until the solution is opalescent, $NaHCO_3$ solution is added to pH 8 5, and then 10 ml of 2-mercapto-ethanol is added dropwise. After stirring at 20° for 2 hours, the reaction solution is stirred into water and the mixture is extracted with ethyl acetate. After drying of the extract over $Na_2SO_4$, it is evaporated and the resulting oily "BOC-Phe-His-Sta-Ile-red-N(FMOC)-Phe-ol" is dissolved in a mixture of 6 ml of piperidine and 15 ml of DMF. The solution is stirred for 1 h, evaporated, and the residue is triturated with ether, purification is carried out by chromatography on Sephadex LH 20, and BOC-Phe-His-Sta-N-[1-(N-(1-hydroxymethyl-2-phenylethyl)-aminomethyl)-2-methylbutyl]amide ("BOC-Phe-His-Sta-Ile-red-Phe-ol"), m.p. 100°–103° is obtained.

The following are obtained analogously from the appropriate His(DNP)-N(FMOC) derivatives:

BOC-Phe-His-Sta-N-[1-(N-(2-phenylethyl)aminomethyl)-3-methylbutyl]amide ("BOC-Phe-His-Sta-Leu-red-NHCH$_2$CH$_2$C$_6$H$_5$"), m.p. 115°–119°
BOC-Phe-His-Sta-N-[1-(N-(2-phenylethyl)aminomethyl)-2-methylbutyl]amide ("BOC-Phe-His-Sta-Ile-red-NHCH$_2$CH$_2$C$_6$H$_5$"), m.p. 110°–115°
BOC-Phe-His-Sta-N-[1-(N-(1-hydroxymethyl-2-phenylethyl)amino-methyl)-3-methylbutyl]amide ("BOC-Phe-His-Sta-Leu-red-Phe-ol"), m.p. 113°–115°
BOC-Phe-His-Sta-N-[1-(N-(1-hydroxymethyl-2-phenylethyl)-aminomethyl)-2,2-dimethylpropyl]amide ("BOC-Phe-His-Sta-tert.-Leu-red-Phe-ol")
BOC-Phe-His-Sta-N-[1-(N-(1-hydroxymethyl-2-phenylethyl)-aminomethyl)-2-methylpropyl]amide ("BOC-Phe-His-Sta-Val-red-Phe-ol"), m.p. 180° (decomposition)
BOC-Phe-His-Sta-N-[1-(N-(2-phenylethyl)aminomethyl)-2-methylpropyl]amide ("BOC-Phe-His-Sta-Val-red-NHCH$_2$CH$_2$C$_6$H$_5$"), m.p. 170°–173°
BOC-Phe-His-Sta-N-[1-(N-(3-phenylpropyl)aminomethyl)-3-methylbutyl]amide ["BOC-Phe-His-Sta-Leu-red-NH-(CH$_2$)$_3$-C$_6$H$_5$"], m.p. 90°–93°
BOC-Phe-His-Sta-N-[1-(N-(2-p-chlorophenylethyl)aminomethyl)-2-methylbutyl]amide ("BOC-Phe-His-Sta-Ile-red-NH-CH$_2$CH$_2$-p-C$_6$H$_4$-Cl")
BOC-Phe-His-Sta-N-[1-(N-(1-hydroxymethyl-2-p-hydroxyphenyl-ethyl)aminomethyl)-2-methylpropyl]amide ("BOC-Phe-His-Sta-Val-red-Tyr-ol")
BOC-Phe-His-Sta-N-[1-(N-(1-hydroxymethyl-2-phenylethyl)aminomethyl)ethyl]amide ("BOC-Phe-His-Sta-Ala-red-Phe-ol");
also
BOC-Phe-His-Sta-Gly-red-Phe-ol
BOC-Phe-His-Sta-Abu-red-Phe-ol
BOC-Phe-His-Sta-NLeu-red-Phe-ol
BOC-Phe-His-Sta-Ile-red-His-ol
BOC-Phe-His-Sta-Ile-red-Trp-ol
BOC-Phe-His-Sta-Ile-red-Tyr-ol
BOC-Phe-His-Sta-Ile-red-NH-CH$_2$-C$_6$H$_5$
BOC-Phe-His-Sta-Ile-red-NH-(CH$_2$)$_3$-C$_6$H$_5$
BOC-Phe-His-Sta-Ile-red-NH-(CH$_2$)$_2$-cyclopropyl
BOC-Phe-His-Sta-Ile-red-NH-(CH$_2$)$_2$-cyclohexyl
BOC-Phe-His-Sta-Ile-red-NH-(CH$_2$)$_2$-p-C$_6$H$_4$-CH$_3$
BOC-Phe-His-Sta-Ile-red-NH-(CH$_2$)$_2$-p-C$_6$H$_4$-OCH$_3$
BOC-Phe-His-Sta-Ile-red-NH-CH$_2$-p-C$_6$H$_4$-F
BOC-Phe-His-Sta-Ile-red-NH-CH$_2$-p-C$_6$H$_4$-Cl
BOC-Phe-His-Sta-Ile-red-NH-(CH$_2$)$_3$-p-C$_6$H$_4$-Cl
BOC-Phe-His-Sta-Ile-red-NH-CH$_2$-p-C$_6$H$_4$-Br
BOC-Phe-His-Sta-Ile-red-NH-(CH$_2$)$_2$-p-C$_6$H$_4$-Br
BOC-Phe-His-Sta-Ile-red-NH-(CH$_2$)$_2$-p-C$_6$H$_4$-I
BOC-Phe-His-Sta-Ile-red-NH-(CH$_2$)$_2$-m-C$_6$H$_4$-CF$_3$
BOC-Phe-His-Sta-Ile-red-NH-(CH$_2$)$_2$-p-C$_6$H$_4$-NH$_2$
BOC-Phe-His-Sta-Ile-red-NH-(CH$_2$)$_2$-(2,4-dimethoxyphenyl)
BOC-Phe-His-Sta-Ile-red-NH-(CH$_2$)$_2$-(3,4-dimethoxyphenyl)
BOC-Phe-His-Sta-Ile-red-NH-(CH$_2$)$_2$-(4-chloro-2-methoxyphenyl)
BOC-Phe-His-Sta-Ile-red-NH-(CH$_2$)$_2$-(2,4-difluorophenyl)
BOC-Phe-His-Sta-Ile-red-NH-(CH$_2$)$_2$-(3,4-difluorophenyl)
BOC-Phe-His-Sta-Ile-red-NH-(CH$_2$)$_2$-(2,4-dichlorophenyl)
BOC-Phe-His-Sta-Ile-red-NH-(CH$_2$)$_2$-(3,4-dichlorophenyl)
BOC-Phe-His-Sta-Ile-red-NH-(CH$_2$)$_2$-(2,4-dibromophenyl)
BOC-Phe-His-Sta-Ile-red-NH-(CH$_2$)$_2$-(3,4-dibromophenyl)
BOC-Phe-His-Sta-Ile-red-NH-(CH$_2$)$_2$-(1-naphthyl)
BOC-Phe-His-Sta-Ile-red-NH-CH$_2$-(4-pyridyl)
BOC-Phe-His-Sta-Ile-red-NH-(CH$_2$)$_2$-(4-pyridyl)
BOC-Phe-His-Sta-Ile-red-NH-(CH$_2$)$_2$-(4-imidazolyl)
BOC-Phe-His-Sta-Ile-red-NH-(4-piperidyl)
BOC-Phe-His-Sta-Ile-red-NH-CH$_2$-(4-piperidyl)
BOC-Phe-His-Sta-Ile-red-NH-(1-benzyl-4-piperidyl)
BOC-Phe-His-Sta-Ile-red-NH-(CH$_2$)$_2$-(1-benzyl-4-piperidyl)
BOC-Phe-His-Sta-Ile-red-NH-(CH$_2$)$_2$-(1-piperazinyl)
BOC-His-Sta-Ile-red-Phe-ol
BOC-Ala-His-Sta-Ile-red-Phe-ol
BOC-Arg-His-Sta-Ile-red-Phe-ol
BOC-Gly-His-Sta-Ile-red-Phe-ol
BOC-His-His-Sta-Ile-red-Phe-ol
BOC-Ile-His-Sta-Ile-red-Phe-ol
BOC-Leu-His-Sta-Ile-red-Phe-ol
BOC-Lys-His-Sta-Ile-red-Phe-ol
BOC-Met-His-Sta-Ile-red-Phe-ol
BOC-Orn-His-Sta-Ile-red-Phe-ol
BOC-Pro-His-Sta-Ile-red-Phe-ol
BOC-Trp-His-Sta-Ile-red-Phe-ol
BOC-Tyr-His-Sta-Ile-red-Phe-ol
BOC-Val-His-Sta-Ile-red-Phe-ol
BOC-Phe-Abu-Sta-Ile-red-Phe-ol
BOC-Phe-Ala-Sta-Ile-red-Phe-ol
BOC-Phe-Arg-Sta-Ile-red-Phe-ol, m.p. 84°–90°
BOC-Phe-Asn-Sta-Ile-red-Phe-ol, m.p. 152°–155°
BOC-Phe-Dab-Sta-Ile-red-Phe-ol
BOC-Phe-Gln-Sta-Ile-red-Phe-ol, m.p. 183°–185°
BOC-Phe-Gly-Sta-Ile-red-Phe-ol
BOC-Phe-Ile-Sta-Ile-red-Phe-ol
BOC-Phe-Leu-Sta-Ile-red-Phe-ol
BOC-Phe-Lys-Sta-Ile-red-Phe-ol
BOC-Phe-Met-Sta-Ile-red-Phe-ol
BOC-Phe-NLeu-Sta-Ile-red-Phe-ol m.p. 112°–118°
BOC-Phe-Orn-Sta-Ile-red-Phe-ol
BOC-Phe-Phe-Sta-Ile-red-Phe-ol
BOC-Phe-Pro-Sta-Ile-red-Phe-ol
BOC-Phe-Trp-Sta-Ile-red-Phe-ol
BOC-Phe-Tyr-Sta-Ile-red-Phe-ol
BOC-Phe-Val-Sta-Ile-red-Phe-ol
BOC-Pro-Phe-His-Sta-Ile-red-Phe-ol
BOC-Pro-Phe-Phe-Sta-Ile-red-Phe-ol
BOC-His-Pro-Phe-His-Sta-Ile-red-Phe-ol
BOC-His-Pro-Phe-Phe-Sta-Ile-red-Phe-ol
BOC-His-Pro-Phe-His-Sta-Ile-red-His-ol
BOC-His-Pro-Phe-His-Sta-Leu-red-Phe-ol
BOC-Phe-His-Sta-Ile-red-Phe-OMe, m.p. 73° (decomposition)
BOC-Phe-His-Sta-Ile-red-Phe-OEt
BOC-Phe-His-Sta-Leu-red-Phe-OMe
BOC-Phe-His-Sta-tert.Leu-red-Phe-OMe
BOC-Phe-His-Sta-Val-red-Phe-OMe
BOC-Phe-His-Sta-Val-red-Tyr-OMe
BOC-Phe-His-Sta-Ala-red-Phe-OMe
BOC-Phe-His-Sta-Gly-red-Phe-OMe
BOC-Phe-His-Sta-Abu-red-Phe-OMe
BOC-Phe-His-Sta-NLeu-red-Phe-OMe
BOC-Phe-His-Sta-Ile-red-His-OMe
BOC-Phe-His-Sta-Ile-red-Trp-OMe
BOC-Phe-His-Sta-Ile-red-Tyr-OMe
BOC-Phe-His-Sta-Ile-red-Gly-OMe, m.p. 90°–92°
BOC-His-Sta-Ile-red-Phe-OMe BOC-Ala-His-Sta-Ile-red-Phe-OMe
BOC-Arg-His-Sta-Ile-red-Phe-OMe
BOC-Gly-His-Sta-Ile-red-Phe-OMe
BOC-His-His-Sta-Ile-red-Phe-OMe
BOC-Ile-His-Sta-Ile-red-Phe-OMe
BOC-Leu-His-Sta-Ile-red-Phe-OMe
BOC-Lys-His-Sta-Ile-red-Phe-OMe
BOC-Met-His-Sta-Ile-red-Phe-OMe
BOC-Orn-His-Sta-Ile-red-Phe-OMe
BOC-Pro-His-Sta-Ile-red-Phe-OMe
BOC-Trp-His-Sta-Ile-red-Phe-OMe
BOC-Tyr-His-Sta-Ile-red-Phe-OMe
BOC-Val-His-Sta-Ile-red-Phe-OMe
BOC-Phe-Abu-Sta-Ile-red-Phe-OMe
BOC-Phe-Ala-Sta-Ile-red-Phe-OMe
BOC-Phe-Arg-Sta-Ile-red-Phe-OMe
BOC-Phe-Asn-Sta-Ile-red-Phe-OMe
BOC-Phe-Dab-Sta-Ile-red-Phe-OMe
BOC-Phe-Gln-Sta-Ile-red-Phe-OMe
BOC-Phe-Gly-Sta-Ile-red-Phe-OMe
BOC-Phe-Ile-Sta-Ile-red-Phe-OMe
BOC-Phe-Leu-Sta-Ile-red-Phe-OMe
BOC-Phe-Lys-Sta-Ile-red-Phe-OMe
BOC-Phe-Met-Sta-Ile-red-Phe-OMe
BOC-Phe-NLeu-Sta-Ile-red-Phe-OMe
BOC-Phe-Orn-Sta-Ile-red-Phe-OMe
BOC-Phe-Phe-Sta-Ile-red-Phe-OMe
BOC-Phe-Pro-Sta-Ile-red-Phe-OMe
BOC-Phe-Trp-Sta-Ile-red-Phe-OMe
BOC-Phe-Tyr-Sta-Ile-red-Phe-OMe
BOC-Phe-Val-Sta-Ile-red-Phe-OMe
BOC-Pro-Phe-His-Sta-Ile-red-Phe-OMe
BOC-Pro-Phe-Phe-Sta-Ile-red-Phe-OMe
BOC-His-Pro-Phe-His-Sta-Ile-red-Phe-OMe
BOC-His-Pro-Phe-Phe-Sta-Ile-red-Phe-OMe
BOC-His-Pro-Phe-His-Sta-Ile-red-His-OMe
BOC-His-Pro-Phe-His-Sta-Leu-red-Phe-OMe
BOC-Phe-His-Sta-Ile-red-Phe-NH₂
BOC-His-Pro-Phe-His-Sta-Ile-red-Phe-NH₂
BOC-Phe-His-Sta-Ile-red-His-NH₂
BOC-Phe-His-Sta-Ile-red-Tyr-NH₂
BOC-Phe-His-Sta-Leu-red-Phe-NH₂
BOC-His-Pro-Phe-His-Sta-Leu-red-Phe-NH₂
BOC-His-Pro-Phe-His-Sta-Leu-red-Tyr-NH₂
BOC-His-Pro-Phe-Phe-Sta-Leu-red-Phe-NH₂
Acetyl-Phe-His-Sta-Leu-red-Phe-ol
Acetyl-Phe-His-Sta-Leu-red-Phe-OMe
Acetyl-Pro-Phe-His-Sta-Leu-red-Phe-NH₂
Acetyl-Phe-His-Sta-Leu-red-Phe-NH₂
Propionyl-Phe-His-Sta-Ile-red-Phe-ol
Isobutyryl-His-Pro-Phe-His-Sta-Ala-red-Phe-NH₂
Isobutyryl-Phe-His-Sta-Ile-red-Phe-ol
Isobutyryl-Phe-His-Sta-Ile-red-Phe-OMe
Isobutyryl-His-Pro-Phe-His-Sta-Ile-red-Phe-ol
Isobutyryl-His-Pro-Phe-His-Sta-Ile-red-Phe-OMe
Isobutyryl-His-Pro-Phe-His-Sta-Ile-red-His-NH₂
Isobutyryl-His-Pro-Phe-His-Sta-Leu-red-Phe-ol
Isobutyryl-His-Pro-Phe-His-Sta-Leu-red-Phe-OMe
Isovaleryl-Phe-His-Sta-Ile-red-Phe-ol
Isovaleryl-Phe-His-Sta-Ile-red-Phe-OMe
Isovaleryl-His-Pro-Phe-His-Sta-Ile-red-Phe-ol
Isovaleryl-His-Pro-Phe-His-Sta-Ile-red-Phe-OMe
Isovaleryl-His-Pro-Phe-His-Sta-Ile-red-His-NH₂
Isovaleryl-His-Pro-Phe-His-Sta-Leu-red-Phe-ol
Isovaleryl-His-Pro-Phe-His-Sta-Leu-red-Phe-OMe
Isovaleryl-His-Pro-Phe-His-Sta-Leu-red-His-NH₂
Isovaleryl-His-Pro-Phe-His-Sta-Leu-red-Phe-NH₂
Trimethylacetyl-Phe-His-Sta-Ile-red-Phe-ol
Isocaproyl-Phe-His-Sta-Ile-red-Phe-ol
Benzoyl-Phe-His-Sta-Ile-red-Phe-ol
Phenylacetyl-Phe-His-Sta-Ile-red-Phe-ol
1-Naphthylacetyl-Phe-His-Sta-Ile-red-Phe-ol
3-Phenylpropionyl-Phe-His-Sta-Ile-red-Phe-ol
3-p-Tolylpropionyl-Phe-His-Sta-Ile-red-Phe-ol
3-o-Methoxyphenylpropionyl-Phe-His-Sta-Ile-red-Phe-ol
3-p-Methoxyphenylpropionyl-Phe-His-Sta-Ile-red-Phe-ol
3-p-Fluorophenylpropionyl-Phe-His-Sta-Ile-red-Phe-ol
3-p-Chlorophenylpropionyl-Phe-His-Sta-Ile-red-Phe-ol
3-p-Bromophenylpropionyl-Phe-His-Sta-Ile-red-Phe-ol
3-p-Iodophenylpropionyl-Phe-His-Sta-Ile-red-Phe-ol
3-m-Trifluoromethylphenylpropionyl-Phe-His-Sta-Ile-red-Phe-ol
3-Cyclohexylpropionyl-Phe-His-Sta-Ile-red-Phe-ol
6-Cycloheptylhexanoyl-Phe-His-Sta-Ile-red-Phe-ol
POA-Phe-His-Sta-Ile-red-Phe-ol
Cyclopropylcarbonyl-Phe-His-Sta-Ile-red-Phe-ol
Cyclopentylcarbonyl-Phe-His-Sta-Ile-red-Phe-ol
Cyclohexylcarbonyl-Phe-His-Sta-Ile-red-Phe-ol
CBZ-Phe-His-Sta-Ile-red-Phe-ol
CBZ-Phe-His-Sta-Ile-red-Phe-OMe
CBZ-His-Pro-Phe-His-Sta-Ile-red-Phe-ol and
CBZ-His-Pro-Phe-His-Sta-Ile-red-Phe-OMe
BOC-Phe-His-NH-CH(CH₂-cyclohexyl)-CHOH-CH₂-CO-Ile-red-Phe-ol
BOC-Phe-NLeu-NH-CH(CH₂-cyclohexyl-CHOH-CH₂-CO-Ile-red-Phe-ol.

EXAMPLE 2

A solution of 1 g of "BOC-Phe-His(BOM)-Sta-Ile-red-N(CH₂C₆H₅)-Phe-ol" [obtainable from "BOC-Ile-red-Phe-ol" by N-benzylation and elimination of the BOC group to give "Ile-red-N(CH₂C₆H₅)-Phe-ol" followed by stepwise synthesis of the peptide chain in analogy to Example 1] in 50 ml of methanol is hydrogenated on 1 g of Pd(OH)₂ at 20° and under 3 bar for 4 hours. The mixture is filtered, the filtrate is evaporated, and "BOC-Phe-His-Sta-Ile-red-Phe-ol" is obtained, m.p. 100°–103°.

The other compounds mentioned in Example 1 can be obtained analogously by hydrogenolysis of the corresponding N-benzyl derivatives, as long as they do not contain other groups which can be eliminated by hydrogenolysis and which are likewise eliminated on hydrogenolysis; thus, for example, Phe-His-Sta-Ile-red-Phe-ol is produced from CBZ-Phe-His-Sta-Ile-red-N(CH₂C₆H₅)-Phe-ol.

EXAMPLE 3

A solution of 1 g of BOC-Phe-His(BOM)-Sta-N-λ1-(N(1-hydroxymethyl-2-(1-BOM-4-imidazolyl)ethyl-)aminomethyl)2-methylbutyl] amide ["BOC-Phe-His(-BOM)-Sta-Ile-red-His(BOM)-ol"; obtainable from BOC-Ile-OH and H-His(BOM)-OMe via BOC-Ile-His(-BOM)-OMe, "BOC-Ile-red-His(BOM)-ol" , "BOC-Ile-red-N(FMOC)-His(BOM)-ol", "Ile-red-N(FMOC)-His(BOM)-ol", "BOC-Sta-Ile-red-N(FMOC)-His(-BOM)-ol", "Sta-Ile-red-N(FMOC)-His-(BOM)-ol", "BOC-His(BOM)-Sta-Ile-red-N(FMOC)-His(BOM)-ol", "His(BOM)-Sta-Ile-red-N(FMOC)-His(BOM)-ol" and "BOC-Phe-His-(BOM)-Sta-Ile-red-N(FMOC)-His (BOM)-ol] and 1 g of ammonium formate in 40 ml of DMF has added to it 1 g of 5% Pd-C, and the mixture is stirred at 20° for 3 hours. It is evaporated, the usual working up is carried out and BOC-Phe-His-Sta-N-[1-(N-(1-hydroxymethyl-2-(4-imidazolyl) ethyl)aminomethyl)-2-methylbutyl] amide ("BOC-Phe-His-Sta-Ile-red-His-ol") is obtained.

The other compounds mentioned in Example 1 can be obtained analogously from the corresponding N-BOM derivatives.

EXAMPLE 4

A solution of 1 g of BOC-Phe-His-Sta-N-[1-(N-(1-hydroxymethyl-2-phenylethyl) iminomethyl)-2-methylbuty] amide (obtainable by condensation of BOC-Phe-His-Sta-Ile- a1 with Phe-ol) in 50 ml of methanol is hydrogenated on 1 g of 5% Pd-C at 20° and under 1 bar until uptake of $H_2$ has stopped. The mixture is filtered, the filtrate is evaporated, and "BOC-Phe-His-Sta-Ile-red-Phe-ol" is obtained, m.p. 100°–103°.

EXAMPLE 5

A solution of 777 mg of the N-[1-(N-(1-hydroxymethyl-2-phenylethyl)aminomethyl)-2-methylbutyl] amide of 3-oxo-4S-(BOC-Phe-His-amino)-5-methylheptanoic acid [obtainable by reaction of "Ile-red-N(FMOC)-Phe-ol" with 3-oxo-4-BOC-amino-5-methylheptanoic acid to give the [1-(N-(1-hydroxymethyl-2-phenylethyl)-N (FMOC)-aminomethyl)-2-methylbutyl] amide of 3-oxo-4S-BOC-amino-5-methylheptanoic acid, elimination of the BOC group to give the 3-oxo-4S-amino compound, reaction with BOC-His(DNP)-OH to give the [1-(N(1-hydroxymethyl-2-phenylethyl)-N (FMOC)-aminomethyl)-2methylbuty] amide of 3-oxo-4S-(BOC-His(DNP)-amino)-5-methylheptanoic acid, elimination of the BOC group to give the 3-oxo-4S-(His(DNP)-amino) compound, condensation with BOC-Phe-OH to give the [1-(N-(1-hydroxymethyl-2-phenylethyl)-FMOC-aminomethyl)-2-methylbuty] amide of 3-oxo-4S-(BOC-Phe-His-amino)-5-methylheptanoic acid and elimination of the DNP and FMOC groups in analogy to Example 1] in 40 ml of methanol at 0° has added to it 200 mg of $NaBH_4$. The mixture is stirred for 2 hours, hydrochloric acid is added to destroy the excess $NaBH_4$, the usual working up is carried out, and a mixture of two stereoisomers is obtained, from which it is possible by chromatography (silica gel) to separate out "BOC-Phe-His-Sta-Ile-red-Phe-ol", m.p 100°–103°.

EXAMPLE 6

A solution of 100 mg of BOC-Phe-His-Sta-N- [1-(N-(1-hydroxymethyl-2-phenylethyl) aminomethyl)-2-methylbutyl] amide ("BOC-Phe-His-Sta-Ile-red-Phe-ol") in 2 ml of 4N HCl in dioxane is stirred at 20° for 30 minutes and is then evaporated. Phe-His-Sta-N-[1-(N-(1-hydroxymethyl-2-phenylethyl)aminomethyl)-2-methylbutyl]amide ("Phe-His-Sta-Ile-red-Phe-ol") is obtained as the hydrochloride.

The following are obtained analogously by cleavage of the corresponding BOC derivatives:
Phe-His-Sta-Leu-red-NHCH$_2$CH$_2$-C$_6$H$_5$
Phe-His-Sta-Ile-red-NHCH$_2$CH$_2$-C$_6$H$_5$
Phe-His-Sta-Leu-red-Phe-ol
Phe-His-Sta-tert.-Leu-red-Phe-ol
Phe-His-Sta-Val-red-Phe-ol
Phe-His-Sta-Val-red-NHCH$_2$CH$_2$-C$_6$H$_5$
Phe-His-Sta-Leu-red-NH-(CH$_2$)$_3$-C$_6$H$_5$
Phe-His-Sta-Ile-red-NH-(CH$_2$)$_2$-p-C$_6$H$_4$-Cl
Phe-His-Sta-Val-red-Tyr-ol
Phe-His-Sta-Ala-red-Phe-ol
Phe-His-Sta-Gly-red-Phe-ol
Phe-His-Sta-Abu-red-Phe-ol
Phe-His-Sta-NLeu-red-Phe-ol
Phe-His-Sta-Ile-red-His-ol
Phe-His-Sta-Ile-red-Trp-ol
Phe-His-Sta-Ile-red-Tyr-ol
Phe-His-Sta-Ile-red-NH-CH$_2$-C$_6$H$_5$
Phe-His-Sta-Ile-red-NH-(CH$_2$)$_3$-C$_6$H$_5$
Phe-His-Sta-Ile-red-NH-(CH$_2$)$_2$-C$_6$H$_5$
Phe-His-Sta-Ile-red-NH-(CH$_2$)$_2$-cyclopropyl
Phe-His-Sta-Ile-red-NH-(CH$_2$)$_2$-cyclohexyl
Phe-His-Sta-Ile-red-NH-(CH$_2$)$_2$-p-C$_6$H$_4$-CH$_3$
Phe-His-Sta-Ile-red-NH-(CH$_2$)$_2$-p-C$_6$H$_4$-OCH$_3$
Phe-His-Sta-Ile-red-NH-CH$_2$-p-C$_6$H$_4$-F
Phe-His-Sta-Ile-red-NH-(CH$_2$)$_2$-p-C$_6$H$_4$-F
Phe-His-Sta-Ile-red-NH-CH$_2$-p-C$_6$H$_4$-Cl
Phe-His-Sta-Ile-red-NH-(CH$_2$)$_3$-p-C$_6$H$_4$-Cl
Phe-His-Sta-Ile-red-NH-CH$_2$-p-C$_6$H$_4$-Br
Phe-His-Sta-Ile-red-NH-(CH$_2$)$_2$-p-C$_6$H$_4$-Br
Phe-His-Sta-Ile-red-NH-(CH$_2$)$_2$-p-C$_6$H$_4$-I
Phe-His-Sta-Ile-red-NH-(CH$_2$)$_2$-m-C$_6$H$_4$-CF$_3$
Phe-His-Sta-Ile-red-NH-(CH$_2$)$_2$-p-C$_6$H$_4$-NH$_2$
Phe-His-Sta-Ile-red-NH-(CH$_2$)$_2$-(2,4-dimethoxyphenyl)
Phe-His-Sta-Ile-red-NH-(CH$_2$)$_2$-(3,4-dimethoxyphenyl)
Phe-His-Sta-Ile-red-NH-(CH$_2$)$_2$-(4-chloro-2-methoxyphenyl)
Phe-His-Sta-Ile-red-NH-(CH$_2$)$_2$-(2,4-difluorophenyl)
Phe-His-Sta-Ile-red-NH-(CH$_2$)$_2$-(3,4-difluorophenyl)
Phe-His-Sta-Ile-red-NH-(CH$_2$)$_2$-(2,4-dichlorophenyl)
Phe-His-Sta-Ile-red-NH-(CH$_2$)$_2$-(3,4-dichlorophenyl)
Phe-His-Sta-Ile-red-NH-(CH$_2$)$_2$-(2,4-dibromophenyl)
Phe-His-Sta-Ile-red-NH-(CH$_2$)$_2$-(3,4-dibromophenyl)
Phe-His-Sta-Ile-red-NH-(CH$_2$)$_2$-(1-naphthyl)
Phe-His-Sta-Ile-red-NH-CH$_2$-(4-pyridyl)
Phe-His-Sta-Ile-red-NH-(CH$_2$)$_2$-(4-pyridyl)
Phe-His-Sta-Ile-red-NH-(CH$_2$)$_2$-(4-imidazolyl)
Phe-His-Sta-Ile-red-NH-(4-piperidyl)
Phe-His-Sta-Ile-red-NH-CH$_2$-(4-piperidyl)
Phe-His-Sta-Ile-red-NH-(CH$_2$)$_2$-(4-piperidyl)
Phe-His-Sta-Ile-red-NH-(1-benzyl-4-piperidyl)
Phe-His-Sta-Ile-red-NH-(CH$_2$)$_2$-(1-benzyl-4-piperidyl)
Phe-His-Sta-Ile-red-NH-(CH$_2$)$_2$-(1-piperazinyl)
His-Sta-Ile-red-Phe-ol
Ala-His-Sta-Ile-red-Phe-ol
Arg-His-Sta-Ile-red-Phe-ol
Gly-His-Sta-Ile-red-Phe-ol
His-His-Sta-Ile-red-Phe-ol
Ile-His-Sta-Ile-red-Phe-ol
Leu-His-Sta-Ile-red-Phe-ol
Lys-His-Sta-Ile-red-Phe-ol
Met-His-Sta-Ile-red-Phe-ol
Orn-His-Sta-Ile-red-Phe-ol
Pro-His-Sta-Ile-red-Phe-ol
Trp-His-Sta-Ile-red-Phe-ol
Tyr-His-Sta-Ile-red-Phe-ol
Val-His-Sta-Ile-red-Phe-ol
Phe-Abu-Sta-Ile-red-Phe-ol
Phe-Ala-Sta-Ile-red-Phe-ol
Phe-Arg-Sta-Ile-red-Phe-ol
Phe-Asn-Sta-Ile-red-Phe-ol
Phe-Dab-Sta-Ile-red-Phe-ol
Phe-Gln-Sta-Ile-red-Phe-ol
Phe-Gly-Sta-Ile-red-Phe-ol
Phe-Ile-Sta-Ile-red-Phe-ol Phe-Leu-Sta-Ile-red-Phe-ol
Phe-Lys-Sta-Ile-red-Phe-ol
Phe-Met-Sta-Ile-red-Phe-ol
Phe-NLeu-Sta-Ile-red-Phe-ol
Phe-Orn-Sta-Ile-red-Phe-ol
Phe-Phe-Sta-Ile-red- Phe-ol
Phe-Pro-Sta-Ile-red-Phe-ol
Phe-Trp-Sta-Ile-red-Phe-ol
Phe-Tyr-Sta-Ile-red-Phe-ol
Phe-Val-Sta-Ile-red-Phe-ol
Pro-Phe-His-Sta-Ile-red-Phe-ol
Pro-Phe-Phe-Sta-Ile-red-Phe-ol
His-Pro-Phe-His-Sta-Ile-red-Phe-ol
His-Pro-Phe-Phe-Sta-Ile-red-Phe-ol
His-Pro-Phe-His-Sta-Ile-red-His-ol
His-Pro-Phe-His-Sta-Leu-red-Phe-ol
Phe-His-Sta-Ile-red-Phe-OMe
Phe-His-Sta-Leu-red-Phe-OMe
Phe-His-Sta-tert.Leu-red-Phe-OMe
Phe-His-Sta-Val-red-Phe-OMe
Phe-His-Sta-Val-red-Tyr-OMe
Phe-His-Sta-Ala-red-Phe-OMe
Phe-His-Sta-Gly-red-Phe-OMe
Phe-His-Sta-Abu-red-Phe-OMe
Phe-His-Sta-NLeu-red-Phe-OMe
Phe-His-Sta-Ile-red-His-OMe
Phe-His-Sta-Ile-red-Trp-OMe
Phe-His-Sta-Ile-red-Tyr-OMe
His-Sta-Ile-red-Phe-OMe
Ala-His-Sta-Ile-red-Phe-OMe
Arg-His-Sta-Ile-red-Phe-OMe
Gly-His-Sta-Ile-red-Phe-OMe
His-His-Sta-Ile-red-Phe-OMe
Ile-His-Sta-Ile-red-Phe-OMe
Leu-His-Sta-Ile-red-Phe-OMe
Lys-His-Sta-Ile-red-Phe-OMe
Met-His-Sta-Ile-red-Phe-OMe
Orn-His-Sta-Ile-red-Phe-OMe
Pro-His-Sta-Ile-red-Phe-OMe
Trp-His-Sta-Ile-red-Phe-OMe
Tyr-His-Sta-Ile-red-Phe-OMe
Val-His-Sta-Ile-red-Phe-OMe
Phe-Abu-Sta-Ile-red-Phe-OMe
Phe-Ala-Sta-Ile-red-Phe-OMe
Phe-Arg-Sta-Ile-red-Phe-OMe
Phe-Asn-Sta-Ile-red-Phe-OMe
Phe-Dab-Sta-Ile-red-Phe-OMe
Phe-Gln-Sta-Ile-red-Phe-OMe
Phe-Gly-Sta-Ile-red-Phe-OMe
Phe-Ile-Sta-Ile-red-Phe-OMe
Phe-Leu-Sta-Ile-red-Phe-OMe
Phe-Lys-Sta-Ile-red-Phe-OMe
Phe-Met-Sta-Ile-red-Phe-OMe
Phe-NLeu-Sta-Ile-red-Phe-OMe
Phe-Orn-Sta-Ile-red-Phe-OMe
Phe-Phe-Sta-Ile-red-Phe-OMe
Phe-Pro-Sta-Ile-red-Phe-OMe
Phe-Trp-Sta-Ile-red-Phe-OMe
Phe-Tyr-Sta-Ile-red-Phe-OMe
Phe-Val-Sta-Ile-red-Phe-OMe
Pro-Phe-His-Sta-Ile-red-Phe-OMe
Pro-Phe-Phe-Sta-Ile-red-Phe-OMe
His-Pro-Phe-His-Sta-Ile-red-Phe-OMe
His-Pro-Phe-Phe-Sta-Ile-red-Phe-OMe
His-Pro-Phe-His-Sta-Ile-red-His-OMe
His-Pro-Phe-His-Sta-Leu-red-Phe-OMe
Phe-His-Sta-Ile-red-Phe-NH$_2$
His-Pro-Phe-His-Sta-Ile-red-Phe-NH$_2$
Phe-His-Sta-Ile-red-His-NH$_2$
Phe-His-Sta-Ile-red-Tyr-NH$_2$
Phe-His-Sta-Leu-red-Phe-NH$_2$
His-Pro-Phe-His-Sta-Leu-red-Phe-NH$_2$
His-Pro-Phe-His-Sta-Leu-red-Tyr-NH$_2$ and
His-Pro-Phe-Phe-Sta-Leu-red-Phe-NH$_2$.

EXAMPLE 7

1 g of "CBZ-Phe-His-Sta-Ile-red-Phe-ol" is dissolved in 10 ml of methanol, hydrogenation is carried out on 0.5 g of 10% Pd-C at 20° and under 1 bar for 3 hours, the mixture is filtered, the filtrate is evaporated, and "Phe-His-Sta-Ile-red-Phe-ol" is obtained.

EXAMPLE 8

A solution of 821 mg of "BOC-Phe-His-Sta-Ile-red-Phe-OEt" in 45 ml of CH$_2$Cl$_2$ at −50° has added to it 350 mg of diisobutylaluminium hydride, and the mixture is stirred for 1 hour. After carrying out the usual working up, "BOC-Phe-His-Sta-Ile-red-Phe-ol" is obtained, m.p. 100°–103°

The examples which follow relate to pharmaceutical formulations.

EXAMPLE A: INJECTION VIALS

A solution of 1 kg of Phe-His-Sta-Ile-red-Phe-ol hydrochloride and 50 g of disodium hydrogen phosphate in 30 of double-distilled water is adjusted to pH 6.5 with 2N hydrochloric acid, filtered to sterilize dispensed into injection vials, freeze-dried under sterile conditions, and sealed sterile. Each injection vial contains 500 mg of active compound.

EXAMPLE B: SUPPOSITORIES

A mixture of 500 g of BOC-Phe-His-Sta-Ile-red-Phe-ol is melted with 100 g of soya lecithin and 1,400 g of cocoa butter, poured into molds and allowed to cool. Each suppository contains 500 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A peptide of the formula $$X-Z-NH-CHR-CHOH-CH_2-CO-NH-CHR^1-CH_2-NH-CHY-C_nH_{2n}-R^2$$

wherein
X is H, $R^3-O-CH_2-CO-$, $R^3-O-CO-$, $R^3-CH_2-O-CO-$ or 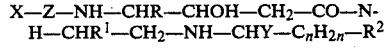,
is 1 to 4 aminoacids bonded together to form a peptide, the amino acids being Abu, Ala, Arg, Asn, Dab, Gln, Gly, His, Ile, Leu, Lys, Met, NLeu, Orn, Phe, Pro, Trp, Tyr or Val,
is A, Ar-C$_{1-4}$-alkyl or cycloalkyl-alkyl of 4–11 C atoms in total,
R$^1$ is H or A,
Y is H, A, $-C_pH_{2p}-OR^4$, $-C_pH_{2p}-NHR^4$, $-COOR^4$, $-CONHR^4$ or $-CONA_2$, R² is A, cycloalkyl of 3-7 C atoms, Ar, pyridyl, indolyl, imidazolyl, piperidyl, N-benzylpiperidyl or piperazinyl, R³ is A, cycloalkyl of 3-7 C atoms or Ar, R⁴ is H, A or cycloalkyl of 3-7 C atoms, A is alkyl of 1-6 C atoms, Ar is phenyl, phenyl substituted by A, AO, F, Cl, Br, I, CF₃, OH or NH₂, or naphthyl, and each of m, n and p independently is 0, 1, 2, 3, 4 or 5, or a salt thereof.

2. A peptide of claim 1, wherein Ar is phenyl or phenyl substituted by one substituent.

3. A peptide of claim 1, wherein all chiral centers have the S-configuration.

4. A peptide of claim 1, wherein each of m and p independently is 0 or 1, and n is 0, 1 or 2.

5. A peptide of claim 1, wherein X is H, POA, alkoxycarbonyl, alkanoyl, cycloalkylcarbonyl, aroyl, arylalkanoyl or cycloalkylalkanoyl.

6. A peptide of claim 1, wherein Z is Phe-His, His, Pro-Phe-His, His-Pro-Phe-His, Abu-His, Ala-His, Ala-Phe, Arg-His, Asn-His, Dab-His, Gln-His, Gly-His, His-His, Ile-His, Leu-His, Lys-His, Met-His, NLeu-His, Orn-His, Phe-Abu, Phe-Ala, Phe-Arg, Phe-Asn, Phe-Dab, Phe-Gln, Phe-Gly, Phe-Ile, Phe-Leu, Phe-Lys, Phe-Met, Phe-NLeu, Phe-Orn, Phe-Phe, Phe-Pro, Phe-Trp, Phe-Tyr, Phe-Val, Pro-His, Trp-His, Tyr-His, Val-His, Pro-Ala-His, Pro-Ala-Phe, Pro-Phe-Ala, Pro-Phe-Phe, His-Pro-Ala-His, His-Pro-Ala-Phe, His-Pro-Phe-Ala or His-Pro-Phe-Phe.

7. A peptide of claim 1, wherein —NH—CHY—$C_nH_{2n}$—R² is

—NH—CH(COOH)—CH₂C₆H₅
—NH—CH(COOCH₃)—CH₂C₆H₅
—NH—CH(COOC₂H₅)—CH₂C₆H₅
—NH—CH(CONH₂)—CH₂C₆H₅
—NH—CH(CH₂OH)—CH₂C₆H₅
—NH—CH(COOH)—CH₂—p-C₆H₄OH
—NH—CH(COOCH₃)—CH₂—p-C₆H₄OH
—NH—CH(COOC₂H₅)—CH₂—p-C₆H₄OH
—NH—CH(CONH₂)—CH₂—p-C₆H₄OH
—NH—CH(CH₂OH)—CH₂—p-C₆H₄OH
—NH—CH(COOH)—CH₂—(4-imidazolyl)
—NH—CH(COOCH₃)—CH₂—(4-imidazolyl)
—NH—CH(COOC₂H₅)—CH₂—(4-imidazolyl)
—NH—CH(CONH₂)—CH₂—(4-imidazolyl)
—NH—CH(CH₂OH)—CH₂—(4-imidazolyl)
—NH—CH(COOH)—CH₂—(3-indolyl)
—NH—CH(COOCH₃)—CH₂—(3-indolyl)
—NH—CH(COOC₂H₅)—CH₂—(3-indolyl)
—NH—CH(CONH₂)—CH₂—(3-indolyl) or,
—NH—CH(CH₂OH)—CH₂—(3-indolyl)

8. A peptide of claim 1, wherein

X is H, alkanoyl having 2-6 C atoms POA, BOC, CBZ, cycloalkylcarbonyl having 6 or 7 C atoms, benzoyl of 3-phenylpropionyl, Z is His, His-His, Phe-Abu, Phe Arg, Phe-Asn, Phe Dab, Phe-Gln, Phe-His, Phe-Leu, Phe-Lys, Phe-Nleu, Phe-Orn, Phe-Phe, Phe-Trp, Phe-Tyr, Pro-His, Pro-Phe, Trp-His, Tyr-His, Pro-Phe-His or His-Pro-Phe-His, R is isobutyl or cyclohexylmethyl, R¹ is H or alkyl having 1-4 C atoms, Y is H,:COOH, COOCH₃, COOC₂H₅, CONH₂ or CH₂OH, n is 0, 1 or 2, and R² is cyclohexyl; phenyl which is unsubstituted or substituted once or twice by methoxy, F, Cl, Br or OH; naphthyl, pyridyl, indolyl, imidazolyl, piperidyl, N-benzylpiperidyl or piperazinyl.

9. A peptide of claim 1, wherein

X is H, BOC or CBZ,

Z is Phe-His, Pro-Phe-His or His-Pro-Phe-His,

R is isobutyl or cyclohexylmethyl,

R¹ is H or alkyl having 1-4 C atoms,

Y is H, COOCH₃, CONH₂ or CH₂O, n is 0, 1 or 2, and

R² is cyclohexyl; phenyl which is unsubstituted or substituted once or twice by methoxy, F, Cl, Br or OH; naphthyl, pyridyl, indolyl, imidazolyl, piperidyl, N-benzylpiperidyl or piperazinyl.

10. A peptide of claim 1, wherein

X is H or BOC,

Z is Phe-His,

R is isobutyl or cyclohexylmethyl,

R¹ is H or alkyl having 1-4 C atoms,

Y is H, COOCH₃, CONH₂ or CH₂O, n is 0, 1 or 2, and

R² is cyclohexyl; phenyl which is unsubstituted or substituted once or twice by methoxy, F, Cl, Br or OH; naphthyl, pyridyl, indolyl, imidazolyl, piperidyl, N-benzylpiperidyl or piperazinyl.

11. A peptide of claim 1, wherein

X is H or BOC,

Z is Phe-His,

R ls isobutyl or cyclohexylmethyl,

R¹ is isopropyl, isobutyl or sec.-butyl,

Y is H or CH₂OH, n is 1, and

R² is phenyl, 4-imidazolyl or p-chlorophenyl.

12. BOC-Phe-His-Sta-N-[1-(1-hydroxymethyl-2-phenyl ethyl-aminomethyl)-2-methylbutyl]amide; or, BOC-Phe-His-Sta-N-[1-(2-phenylethylaminomethyl)-2-methylbutyl]amide, each a compound of claim 1.

13. A pharmaceutical composition comprising a compound of claim 1, and a compatible carrier.

14. A composition of claim 13, wherein the amount of said compound is 100 mg to 30 g.

15. A composition of claim 13, wherein the amount of said compound is 500 mg to 5 g.

16. A method of treating or preventing hypertension comprising administering a compound of claim 1.

17. A method of treating or preventing hyperaldosteronism comprising administering a compound of claim 1.

18. A method of treating or preventing a disease contributed to by renin, comprising administering a compound of claim 1.

19. A compound of the formula

X—Z—NH—CHR—CHOH—CH²—$_C$O—NH—CHR¹—CH₂—NQ—CHY—$C_nH_{2n}$—R² wherein

Q is an amino protective group and

X is H, R³—O—CH₂—CO—M R³—O—CO—,R³—CH₂—O—CO— or R³—$C_mH_{2m}$—CO—,

Z is 1 to 4 aminoacids bonded together to form a peptide, the amino acides being Abu, Ala, Arg, Asn, Dab, Gln, Gly, His, Ile, Leu, Lys, Met, NLeu, Orn, Phe, Pro, Trp, Tyr or Val, R is A, Ar-$C_{1-4}$-alkyl or cycloalkyl-alkyl of 4-11 C atoms in-total, R¹ is H or A, Y H, is A, —$C_pH_{2p}$—OR⁴,—$C_pH_{2p}$—NHR⁴,—COOR⁴,—CONHR⁴ or —CONA₂, R² is A, cycloalkyl of 3-7 atoms, Ar, pyridyl, indolyl, imidazolyl, piperidyl, N-benzlpiperidyl or piperazinyl, and n is 0, 1, 2, 3, 4 or 5.

* * * * *